United States Patent

Bolza-Schünemann et al.

[11] Patent Number: 6,111,261
[45] Date of Patent: Aug. 29, 2000

[54] PROCESS AND DEVICE FOR ASSESSING THE QUALITY OF PROCESSED MATERIAL

[75] Inventors: Claus August Bolza-Schünemann; Johannes Georg Schaede, both of Würzburg, Germany

[73] Assignee: Koenig & Bauer Aktiengesellschaft, Wurzburg, Germany

[21] Appl. No.: 09/142,181
[22] PCT Filed: Apr. 1, 1997
[86] PCT No.: PCT/DE97/00654
§ 371 Date: Sep. 30, 1998
§ 102(e) Date: Sep. 30, 1998
[87] PCT Pub. No.: WO97/37329
PCT Pub. Date: Oct. 9, 1997

[30] Foreign Application Priority Data

Apr. 2, 1996 [DE] Germany ............ 196 13 082

[51] Int. Cl.[7] ................................ G01N 21/86
[52] U.S. Cl. .................. 250/559.08; 250/559.46; 356/429
[58] Field of Search ............. 250/559.01, 559.04, 250/559.07, 559.08, 559.44, 559.46, 223 R; 356/375, 376, 429

[56] References Cited

U.S. PATENT DOCUMENTS 4,532,430  7/1985  Ross et al. ........... 250/559.17
4,715,715  12/1987  Howarth et al. .

FOREIGN PATENT DOCUMENTS 527453B  8/1992  European Pat. Off. .
0537513A  4/1993  European Pat. Off. .
0658721A  6/1995  European Pat. Off. .
3136849A  3/1983  Germany .
3413838A  10/1984  Germany .
3637874C  5/1988  Germany .
4033588A  10/1990  Germany .
4123916A  1/1992  Germany .
4103832A  8/1992  Germany .

Primary Examiner—Seungsook Ham
Assistant Examiner—Kevin Pyo
Attorney, Agent, or Firm—Jones, Tullar & Cooper, P.C.

[57] ABSTRACT

The quality of printed, processed material is assessed by passing the processed material through an inspection device. The material for inspection is illuminated with directional light beams. The light rays reflected from the processed material are reflected almost completely into a CCD camera.

8 Claims, 4 Drawing Sheets

PROCESS AND DEVICE FOR ASSESSING THE QUALITY OF PROCESSED MATERIAL

FIELD OF THE INVENTION

The present invention relates to a process and a device for the qualitative assessment of processed material.

DESCRIPTION OF THE PRIOR ART

U.S. Pat. No. 715,715 discloses a device for measuring the color of a material by means of an illumination device and a sensor for spectral analysis.

DE 41 23 916 A1 describes a device for detecting characteristics of an object. In this prior art device, the object is illuminated through a lens in such a way that the reflection angle condition is met for all points on a flat object surface.

EP 0 527 453 B1 discloses a device for the qualitative assessment of printed material by means of an illuminating device and a CCD camera.

The invention is based on the object of providing a process and a method for the qualitative assessment of processed material.

In accordance with the invention, this object is attained by providing a process and an apparatus for the qualitative assessment of processed material, such as printed materials. At least one illuminating device, one photoelectric sensor, and an evaluating device are used. The several components are arranged so that all image areas of the materials to be inspected reflect light beams almost completely onto the sensor. This may be accomplished by deforming the processed material or by breaking the light image of the material being inspected down into a plurality of pixels which can be analyzed individually.

It is possible in an advantageous manner by means of the process, or respectively the device of the present invention to detect reflecting areas in the material to be inspected.

The illuminating device of the device of the present invention is embodied in a space-saving manner by its V-shaped cross section. The extension of the illuminating device transversely to the transport direction of the material to be inspected is minimized in this way.

The length of the illuminating device in the longitudinal direction is also short, since the material to be inspected is very advantageously guided along a curved guide surface. Because of this curvature, the sheet to be inspected is additionally stabilized.

Because of shutters placed on the illuminating device, preferably only light beam directed to the reflecting areas are active, which are reflected almost totally by the reflecting areas of the material to be inspected into the CCD area camera.

By means of these embodiments of the illuminating device and the guide surface, scattered light effects, for example are reduced, and a directed beam path in the illuminating device is created.

BRIEF DESCRIPTION OF THE DRAWINGS

The device of the invention is represented in the drawings and will be described in greater detail in what follows.

Shown are in.

DESCRIPTION OF THE INVENTION

Figure 1:
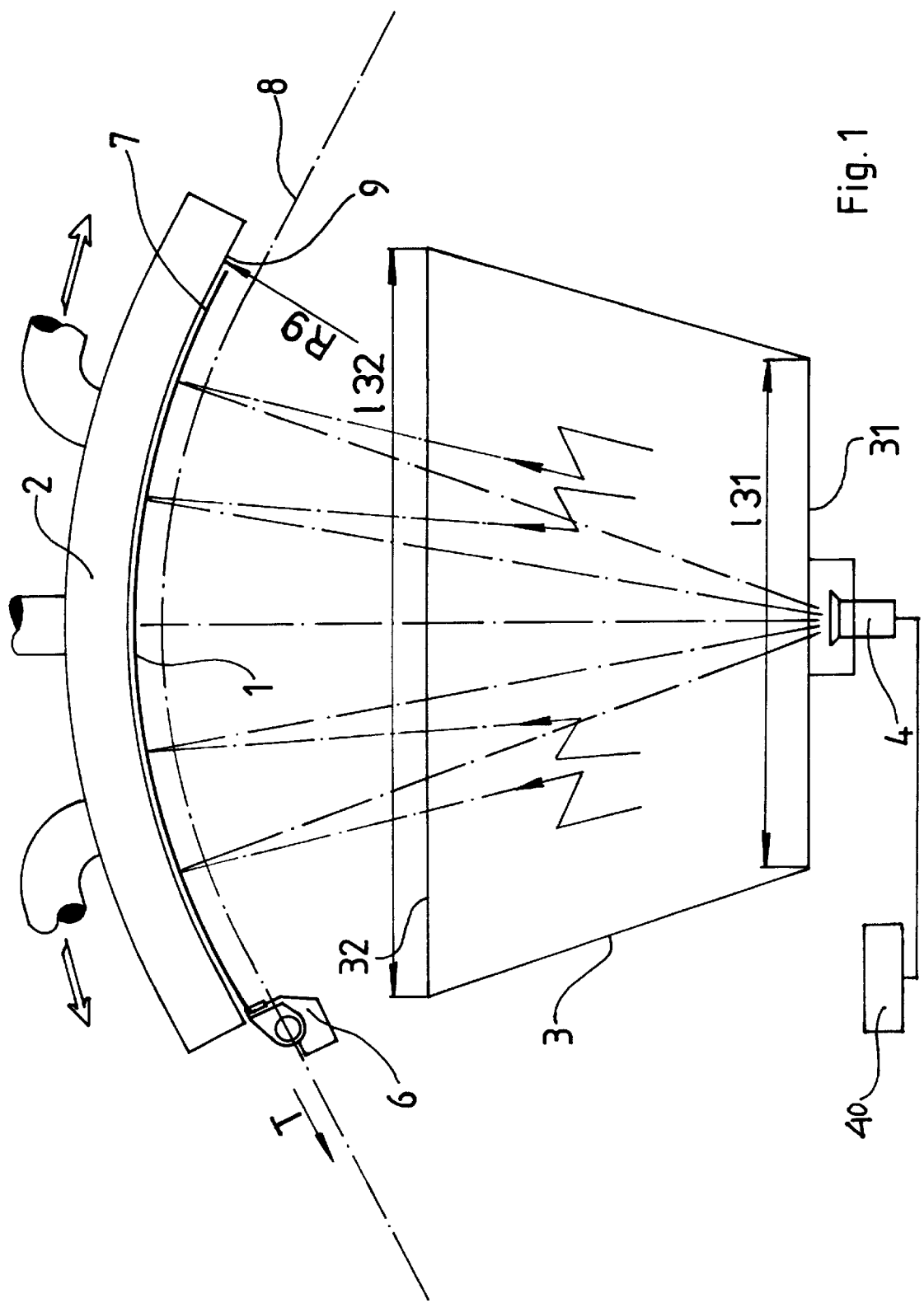
FIG. 1, a schematic lateral view of a device for the qualitative assessment of printed sheets, FIG. 2, a schematic plan view of a device for the qualitative assessment in the transporting direction of the printed sheets, FIG. 3, a schematic view from above on a suction box of the device for the qualitative assessment of printed sheets, FIG. 4, a perspective plan view of the device.

A device, in accordance with the present invention, for the qualitative assessment of processed material 1 essentially consists of a guide 2, an illuminating device 3, at least one sensor 4 and a downstream connected evaluation device, as depicted in FIG. 1.

This quality control system can be employed for monitoring of both webs and sheets 1 in a rotary printing press or a machine for further processing. In the present preferred embodiment, the quality control system is employed in a sheet-fed rotary printing press for accomplishing the qualitative assessment of processed materials in the form of stocks and bonds, in particular for banknotes.

For example, sheets 1 to be inspected are conveyed by means of gripper systems 6 on a sheet transport level 7. These gripper systems 6 are fastened to circulating chains 8 of a chain conveyor, which is known per se. The guide 2 is arranged above the sheet transport level 7. This guide 2 has a shape which, for example, is curved in the transport direction T on its guide surface 9 facing the sheets 1. This guide surface 9 therefore is concavely curved in the transport direction T and has a radius of curvature R9, for example R9=800 mm. The guide 2 is embodied as a suction box 2, for example. To this end, the guide surface 9 is provided with a plurality of perforations 11, i.e. the guide surface 9 is constituted by a perforated plate. The perforations 11 have a diameter of 2 mm, for example, and are distanced from each other in a grid at a distance of 3 mm. This guide surface 9 is arranged to be interchangeable with other guide surfaces 9 that are provided with different perforations and can be folded down for maintenance work.

Figure 3:
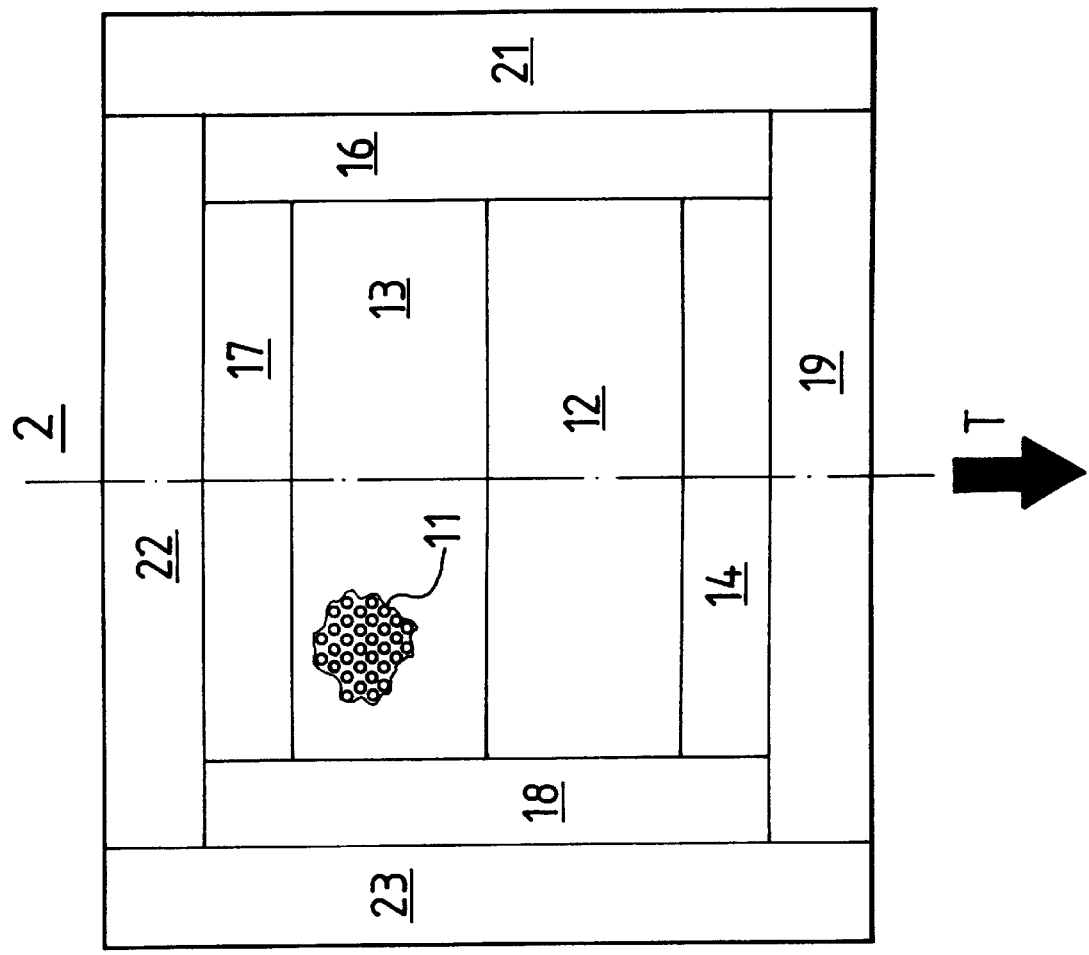

Separating walls, which are not specifically shown are arranged inside the suction box 2, so that a number of suction chambers 12,14,16–19 and 21 23 are formed as seen in FIG. 3. These suction chambers act independently and are separately controllable. An area in the center of the suction box 2 which approximately corresponds to the smallest format of the sheets 1 is divided in the transport direction T into a front 12 and rear suction chamber 13. Respective further suction chambers 14, 16, 17, 18 adjoin the four sides of this interior rectangular area. Again, four outer suction chambers 19, 21, 22, 23 are arranged next to these intermediate suction chambers 14, 16, 17, 18 in the direction of outside edges of the sheet 1. The outermost suction chambers 21, 23 extending in the transport direction T can be once again divided.

A vacuum in each of the individual suction chambers 12 4, 16–19 and 21 23 can be individually controlled, for example by means of a bypass control. In this way, it is possible to adapt a holding force acting on the sheets 1 to the format, material or type of processing of the sheets, for example.

Figure 2:
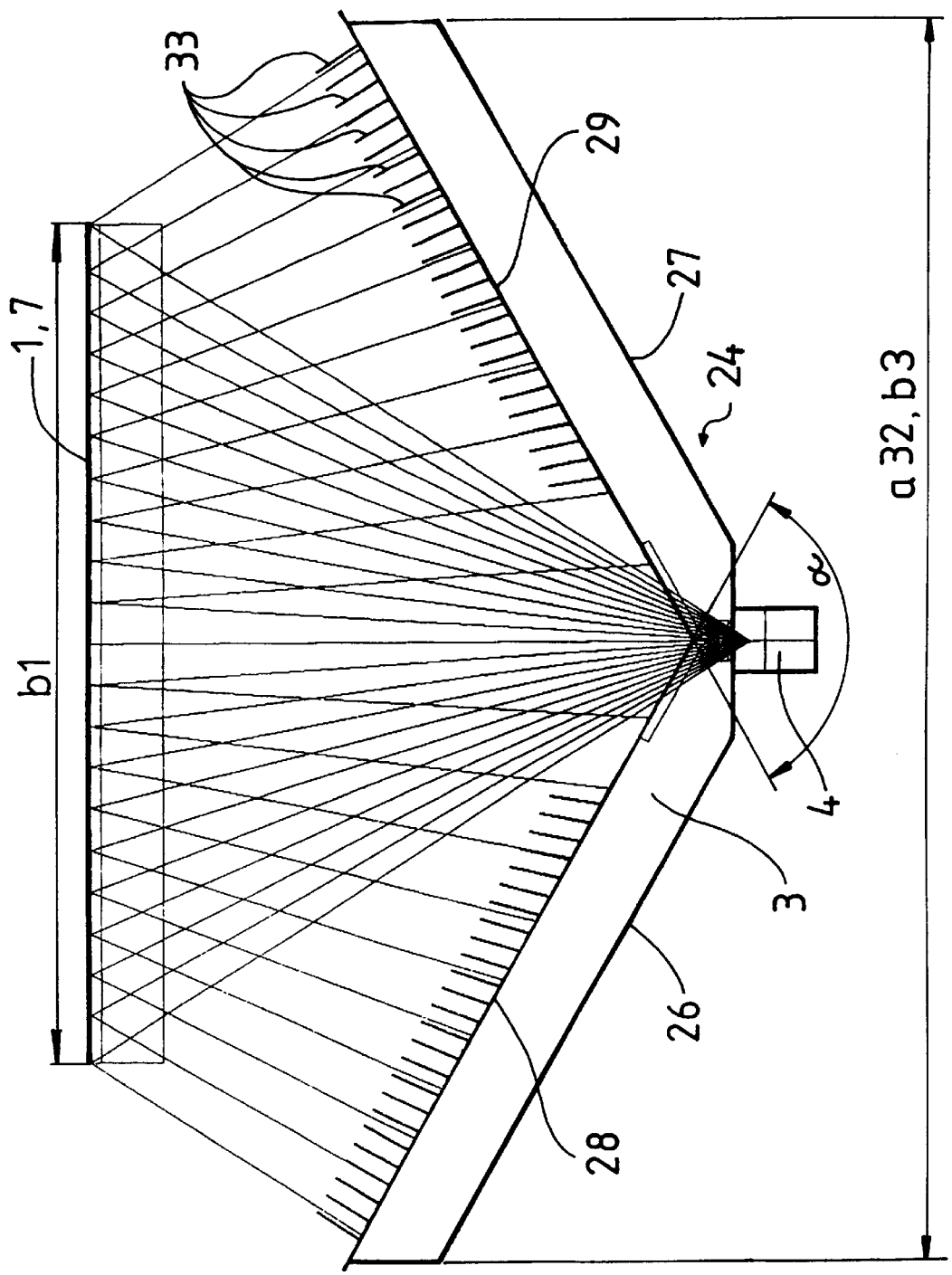

The illuminating device 3 and the sensor 4 are arranged opposite the suction box 2. As shown in more detail in FIG. 2, the illuminating device 3 has a V-shaped cross section in the transport direction T, i.e. it is designed as a V-shaped box 24. This box 24 has two legs 26, 27 with level light outlet surfaces 28, 29 facing the sheets to be inspected. These legs 26, 27 include an opening angle alpha of, for example, 122°. This opening angle alpha preferably has a range between 90° to 150°. Each one of the two light outlet surfaces 28, 29 is shaped trapezoidally as seen in FIG. 1. Here the shorter ones of the two base sides of each trapezoidally shaped surface 26 and 27 meet and extend parallel in respect to the transport direction T. The two short base sides, each have a length 131 of, for example 350 mm. The two larger base sides 32, each of a length 132, for example 132=560 mm, also extend parallel in the transport direction T and are spaced apart transversely to the transport direction T at a distance a32, as seen in FIG. 2 for example a32=1220 mm, which corresponds to a width b3 of the illuminating device. This distance a32 is greater than a greatest width b1, for example 840 mm, of the sheets 1 to be inspected.

The size and format of the illuminating device is matched to the format of the sheets to be inspected. The light outlet surfaces 28, 29 consist of panes of frosted glass, for example. A plurality of diffusely radiating light sources has been respectively arranged underneath these frosted glass panels. These light sources are embodied as single flashtubes, for example. A particularly even illumination of the sheets 1 to be inspected is achieved by this arrangement of light sources and frosted glass panes.

In place of the V-shaped cross section, the illuminating device 3 can also have a curved cross section. This curved cross-section can be for example, in the shape of an arc of a circle.

A plurality of light guide strips 33 (or shutters) extending parallel to the transport direction T can also be placed on the frosted glass panel. These guide strips 33 can be made of sheet metal or also of frosted glass, for example. An angle of inclination of these guide strips 33 in respect to the light outlet surfaces 28, 29, or respectively the sheet transport level 7 is matched to extend parallel with a light beam, wherein such a light beam directed between two guide strips 33 impinges on the sensor 4 after having been reflected on a reflecting area of the sheet 1.

Figure 4:
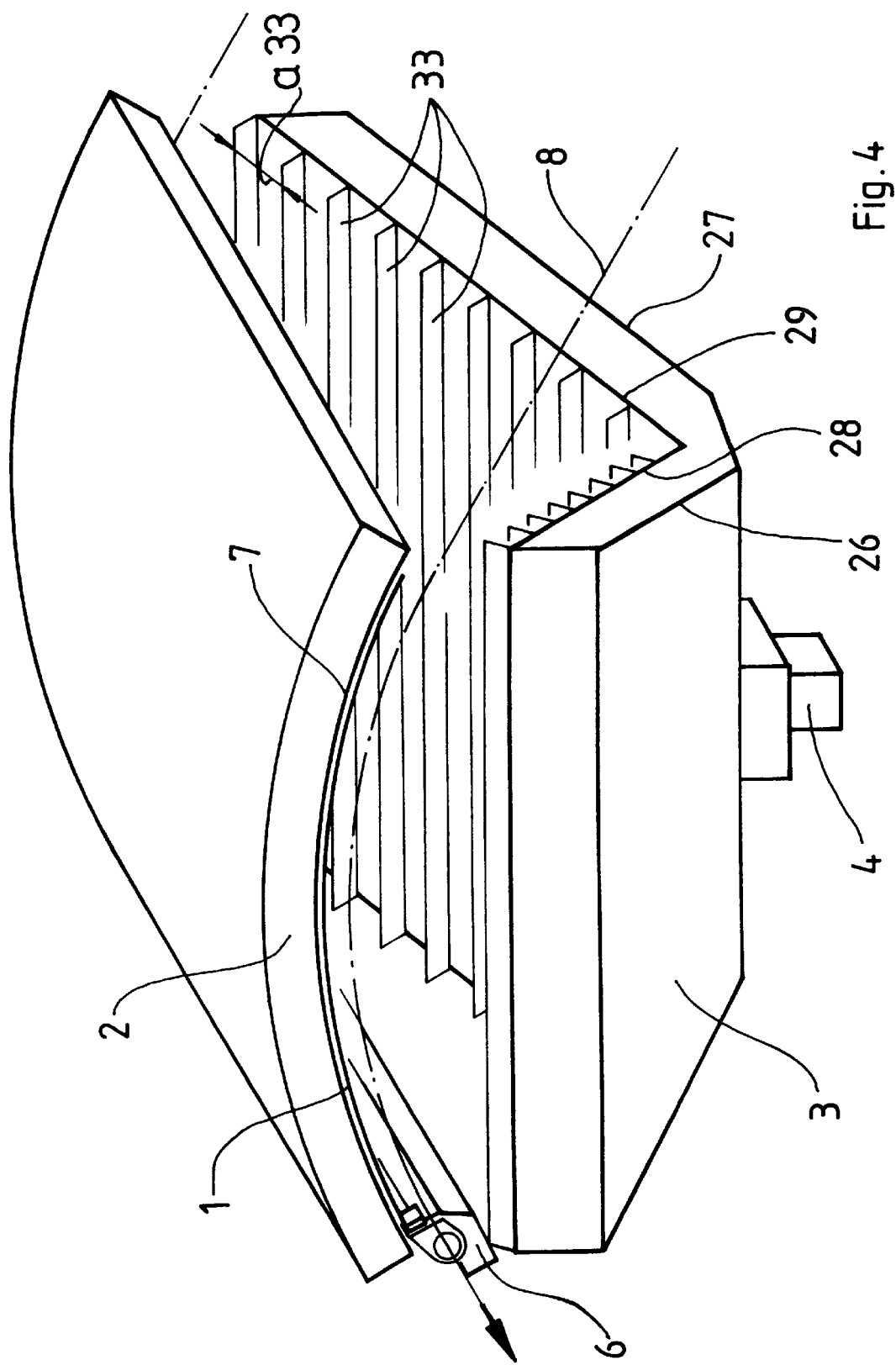

These light guide strips 33 have a spacing distance a33, for example a33=20 mm, from each other. The light guide strips 33 can be seen most clearly in FIGS. 2 and 4.

The illuminating device can also consist of several, singly arranged light sources.

The sensor 4 is arranged in the center and at the apex of this illuminating device 3. In this case a CCD area camera 4 with a lens fixed in front of it is provided as the sensor 4. In the present invention the lens of the server 4 has been designed in such a way that the entire sheet 1 to be inspected is covered, i.e. a distance between the CCD area camera 4 and the sheet transport level 7 is adapted to the lens of the CCD area camera. However, it is also possible to cover several portions of the sheet 1 individually one after the other and to combine them into a whole image. The sheet 1 to be inspected is located in the optical axis of the objective of the CCD area camera 4.

In the present invention a sensor, which is not specifically represented, and which acts as a trigger, has been installed in the suction box. This sensor detects the front edge of the sheet 1 to be inspected and triggers the inspection process. This sensor is arranged displaceably in the transport direction T in order to align with the position of the sheet in case of sheet formats of different sizes in such a way that the inspection of each sheet takes place approximately centered in respect to the lens of the CCD area camera 4.

An evaluation device 40 is connected downstream of the CCD area camera 4. The evaluation device 40 is of a type generally known in the art.

An image of the sheet 1 to be inspected is divided into a matrix consisting of a multitude of small image elements, i.e. pixels. Each one of these pixels is assigned a defined position by providing its coordinates in the X and Y direction of a Cartesian coordinate system. In addition, a value Z is assigned to its remission value, for example its gray scale value, which value Z defines the latter. Each pixel $P_i$ ($X_i$, $Y_i$, $Z_i$) is therefore exactly defined in its position and size by the statement of the values $X_i$, $Y_i$, $Z_i$.

The light image reflected from the sheet 1 to the individual pixels $P_i$ is converted corresponding to its strength by the CCD area camera 4 into an electrical analog signal. This analog signal is supplied to an A/D converter, which forms the digital values $Z_i$ from this. Customarily the value range is here divided into 0 to 255 discrete values. In this case the value 0 means no reflection at all impinging on the corresponding pixel $P_i$ of the CCD area camera 4, while 255 corresponds to a maximum reflection.

In the case of the present invention, the sheet 1 to be inspected has reflecting surfaces. In this connection, "reflecting" is understood to mean that light beams impinging on the reflecting surfaces are reflected with little scattering and have a noticeably directed portion. Such reflecting surfaces can be silver threads in bank notes in particular, or holograms or kinegrams, i.e. security characteristics. These reflecting surfaces are to be recognized as such.

A value range is now assigned to the values of the pixels $P_i$ of such a sheet 1 in such a way that the occurring value range outside of the reflecting surfaces clearly lies within the limits 0 to 255. In actual use, for example, the color "white" is assigned a value $Z_i$ from 180 to 200, and the color "black" a value $Z_i$ between 10 and 30.

This assignment is performed, for example, by adjusting the brightness of the illuminating device 3, the amplification of the camera signal in the electronic evaluation device 40 or of a shutter of the lens of the CCD area camera 4.

The sheet 1 is evenly illuminated by means of the illuminating device 3 in such a way that each reflecting surface located at any arbitrary place on the sheet 1, which has almost ideal reflecting properties, reflects an incident light beam directly into the CCD area camera 4 ("total reflection"). At least partially directed light beams are used for this. The associated value $Z_1$ of a pixel $P_i$ assumes a value upon reflection, which clearly differs from a value assigned to the color "white". For example, in that case the value $Z_i$ of a pixel $P_i$ assigned to a reflecting surface then reaches 230 to 255.

In this way, areas with reflecting surfaces are clearly defined by means of the association of extreme values $Z_i$, i.e. area which weakly scatter and which reflect with clearly directed portions are differentiated from areas with diffuse reflection.

The pixels assigned to the reflecting surfaces are then recognized as such by the electronic evaluation device and are further processed accordingly.

While a preferred embodiment of a process and a device for assessing the quality of processed material in accordance with the present invention has been set forth fully and completely hereinabove, it will be apparent to one of skill in the art that a number of changes in, for example, the type of printing equipment being used, the source of supply of the vacuum for the suction box and the like can be made without departing from the true spirit and scope of the present invention which is accordingly to be limited only by the following claims.

What is claimed is:

1. A process for the qualitative assessment of processed materials including:

providing at least one illuminating device for illuminating material to be assessed with light beams;

providing at least one photoelectric sensor for receiving reflected light beams directed against material to be assessed from said illuminating device;

providing an evaluating device cooperating with said photoelectric sensor;

providing reflecting surfaces which reflect light beams with a noticeably directed portion in said material to be assessed;

arranging the material to be assessed so that light beams reflected from said reflecting surfaces are directed almost completely onto said sensor; and reversibly deforming the material to be assessed for creating a required reflection angle of said light beams.

2. The process in accordance with claim 1 further including providing said at least one photoelectric sensor as a CCD area camera.

3. The process in accordance with claim 1 further including guiding material to be assessed along a curved guide surface.

4. A process for the qualitative assessment of material including:

providing at least one illuminating device for illuminating the material to be assessed;

providing at least one photoelectric sensor for receiving reflected light beams directed against the material to be assessed from said illuminating device;

providing an evaluating device cooperating with said photoelectric sensor;

imprinting the material to be assessed and providing the material with at least one security characteristic providing a weakly scattering image area which reflects light beams with a noticeably directed portion;

arranging said material to be assessed, said illuminating device and said sensor to provide light beam reflection angles from weakly scattering image area of the material to be assessed which direct reflected light beams almost completely into said sensor; and using said almost completely reflected light beams to detect said security characteristic.

5. A device for the qualitative assessment of processed material comprising:

at least one illuminating device for generating light beams;

at least one photoelectric sensor for receiving reflected light beams;

an evaluating device connected to said photoelectric sensor; and at least two generally planar light outlet surfaces on said illuminating device, said light outlet surfaces forming a generally V-shaped illuminating device having a width greater than a greatest width of the processed material to be assessed, said illuminating device and said sensor being arranged for determining a reflection angle of light beams generated by said illuminating device and striking an almost ideally reflecting image area of the material such that there is an almost total reflection of light beams impinging on said image area onto said sensor.

6. A device for the qualitative assessment of processed materials comprising:

at least one illuminating device for generating light beams;

at least one photoelectric sensor for receiving reflected light beams;

an evaluating device connected to said photoelectric sensor;

at least one light outlet surface on said illuminating device;

a plurality of light guide strips on said at least one light outlet surface, said light guide strips being generally parallel with said light beams generated by said at least one illuminating device; and almost ideally reflecting image areas on the processed material, said image areas and said illuminating device and said sensor being arranged to determine a reflected angle which causes an almost total reflection of said light beam striking said image areas onto said sensor.

7. A device for the qualitative assessment of processed material comprising:

at least one illuminating device for generating light beams;

at least one photoelectric sensor for receiving reflected light beams;

an evaluating device connected to said photoelectric sensor;

a curved guide surface for guiding a processed material into a path of said light beams from said illuminating device; and almost ideally reflecting image areas on the processed material, said image areas, said illuminating device, and said sensor being arranged to determine a reflective angle which causes an almost total reflection of said light beams striking said image areas onto said sensor.

8. A process for the qualitative assessment of processed materials including:

providing at least one illuminating device for illuminating materials to be assessed with light beams;

providing at least one photoelectric sensor for receiving reflected light beams directed against material to be assessed from said illuminating device;

providing an evaluating device cooperating with said photoelectric sensor;

providing reflecting surfaces which reflect light beams with a noticeably directed portion in said material to be assessed;

arranging the material to be assessed so that light beams reflected from said reflecting surfaces are directed almost completely onto said sensor; and breaking down an image of the material to be assessed into a plurality of pixels and assigning a value, during reflection to said pixels which differs from a value assignment to the color white.

* * * * *